United States Patent [19]

Stein

[11] 4,324,897
[45] Apr. 13, 1982

[54] 1,2,3 OXADIAZOLIUM SALTS

[75] Inventor: Reinhardt P. Stein, Audubon, Pa.

[73] Assignee: American Home Products Corporation, New York, N.Y.

[21] Appl. No.: 264,892

[22] Filed: May 18, 1981

Related U.S. Application Data

[63] Continuation-in-part of Ser. No. 193,043, Oct. 2, 1980, Pat. No. 4,289,885.

[51] Int. Cl.$^3$ .................. C07D 413/06; C07D 271/04
[52] U.S. Cl. .................................. 548/125; 544/367; 544/138; 546/209
[58] Field of Search ............... 544/138, 367; 546/209; 548/125

[56] References Cited

U.S. PATENT DOCUMENTS 3,277,108  10/1966  Daeniker ............................ 548/125

OTHER PUBLICATIONS

Kikucki et al., *Jap. J. Pharmac.*, vol. 20, (1970), pp. 23-43.

*Primary Examiner*—Henry R. Jiles
*Assistant Examiner*—R. W. Ramsuer
*Attorney, Agent, or Firm*—Richard K. Jackson

[57] ABSTRACT

The disclosed [[2-(substituted amino)-2-phenylethyl]-nitrosoamino]acetonitrile derivatives and the ring closed oxadiazolium salts thereof as well as their pharmaceutically acceptable acid addition salts are antihypertensive agents useful in the treatment of hypertension.

3 Claims, No Drawings

1,2,3 OXADIAZOLIUM SALTS

RELATED APPLICATIONS

This application is a continuation-in-part of U.S. application Ser. No. 193,043, filed Oct. 2, 1980 by Reinhardt P. Stein now U.S. Pat. No. 4,289,885.

BACKGROUND OF THE INVENTION

It has been suggested by Kikuchi et al. Jap. J. Pharmac. 20 23–43 (1970) that sydnonimines containing an amine in 3-position produce hypotension while sydnonimines containing an alkyl, cycloalkyl or dialkylaminoalkyl group in 3-position produce hypertension.

DESCRIPTION OF THE INVENTION

In accordance with this invention there is provided a group of 5-amino-3-[2-substituted amino)-2-phenylethyl]-1,2,3-oxadiazolium salts and [[2-(substituted amino)-2-phenylethyl]nitrosoamino]acetonitrile derivatives which are antihypertensive agents useful in the treatment of hypertension.

The oxadiazolium salts of this invention are also useful as intermediates in the production of 3-[2-(dimethylamino)-2-phenylethyl]-N-[(phenylamino)carbonyl]-sydnone imine derivatives disclosed and claimed in copending application Ser. No. 193,043, filed Oct. 2, 1980 now U.S. Pat. No. 4,289,885.

The oxadiazolium salts of this invention are represented by the following structural formula:

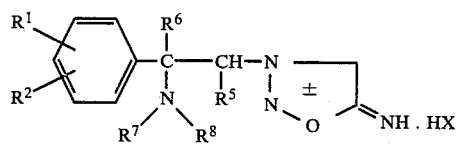

in which
- $R^1$ and $R^2$ are, independently, hydrogen, alkyl of 1 to 6 carbon atoms, alkoxy of 1 to 6 carbon atoms, halo, perfluoroalkyl of 1 to 3 carbon atoms, nitro, alkanoyl of 2 to 4 carbon atoms, or alkoxycarbonyl of 2 to 4 carbon atoms;
- $R^5$ and $R^6$ are, independently, hydrogen or methyl;
- $R^7$ and $R^8$ are, independently, alkyl of 1 to 4 carbon atoms, or when taken with the nitrogen atom to which they are attached, form a piperidinyl, pyrrolidinyl, morpholinyl, N-alkyl piperazinyl in which the alkyl group contains from 1 to 6 carbon atoms or N-phenylpiperazinyl group; and
- X is the anion of a strong acid having a pKa below 2.

The oxadiazolium salts of this invention revert to the corresponding nitroso-nitrile precursor via a pH dependent ring opening. Ring opening occurs rapidly under basic conditions and slower in mild acid, in essence demonstrating the reverse of the ring closing accomplished with strong acids. The nitroso-nitriles are, both intermediates for the antihypertensive oxadiazolium salts and active antihypertensive agents in their own right.

Thus, in accordance with this invention there is also provided a group of nitroso-nitriles useful as antihypertensive agents and in the production of oxadiazolium antihypertensive salts, of the formula:

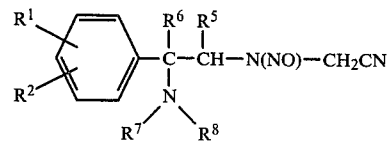

in which
- $R^1$ and $R^2$ are, independently, hydrogen, alkyl of 1 to 6 carbon atoms, alkoxy of 1 to 6 carbon atoms, halo, perfluoroalkyl of 1 to 3 carbon atoms, nitro, alkanoyl of 2 to 4 carbon atoms, or alkoxycarbonyl of 2 to 4 carbon atoms;
- $R^5$ and $R^6$ are, independently, hydrogen or methyl;
- $R^7$ and $R^8$ are, independently, alkyl of 1 to 4 carbon atoms, or when taken with the nitrogen atom to which they are attached, form a piperidinyl, pyrrolidinyl, morpholinyl, N-alkyl piperazinyl in which the alkyl group contains from 1 to 6 carbon atoms or N-phenylpiperazinyl group;

or a pharmaceutically acceptable salt thereof.

In the preceding structural formulae, it is generally preferred that the halo substituent be chlorine, bromine or fluorine although iodine is acceptable. Likewise, it is preferred that the alkyl and alkoxy substituents be relatively small, the methyl, ethyl, propyl, isopropyl, methoxy, ethoxy, propoxy and isopropoxy groups being preferred.

The pharmaceutically acceptable acid addition salts of the compounds of this invention are conventionally produced by the method and from any of the acids disclosed in U.S. Pat. No. 3,277,108, which exhibit a pKa below 2. The salt is preferably that formed during cyclization of the nitrosonitrile, such as with hydrochloric, hydrobromic, sulfuric, phosphoric, methane sulfonic, p-toluene sulfonic acid, and the like. The anion can be replaced with a desired anion by ion exchange chromatography following conventional procedures. The salts formed with the aminic bases of this invention are generally water soluble, dissociating sufficiently to dissolve in aqueous medium to provide a homogeneous solution. Thus, the compounds of this invention may be formulated for administration in aqueous vehicle for practical dosing to reduce blood pressure in patients unable to receive treatment orally.

The compounds of this invention contain one chiral center when $R^5$ is hydrogen and two chiral centers when $R^5$ is methyl. Thus, depending upon the identity of the substituent $R^5$, there is obtained either one or two racemic mixtures of product. The epimers and optical isomers are readily separable by standard techniques well known to the chemist. By selection of the desired starting material, the product can be limited to a single racemic mixture of isomers.

The oxadiazolium salts and the nitroso-nitriles of this invention are prepared by conventional techniques employed in the preparation of sydnonimines.

The starting materials are either known or preparable by routine synthetic methods. Thus, a properly substituted 2-tertiary amino-2-phenylethyl amine is cyanomethylated with a reactant XCH$_2$CN where X may be —OH, —Br, —Cl, tosyl, and the like to form the intermediate

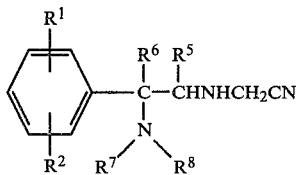

which is nitrosated with an excess of NaNO$_2$ in aqueous HCl to yield the nitroso-nitrile

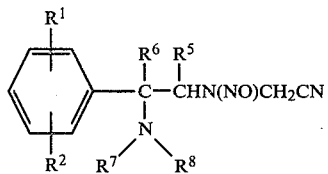

which is then reacted with excess strong acid to form the oxadiazolium salt.

The following example illustrates the preparation of d,l-[[2-(dimethylamino)-2-phenylethyl]nitrosoamino]acetonitrile and its use as an intermediate in the production of d,l-5-amino-3-[2-(dimethylamino)-2-phenylethyl]-1,2,3-oxadiazolium chloride.

EXAMPLE dl-5-Amino-3-[2-(dimethylamino)-2-phenylethyl]-1,2,3-oxadiazolium chloride

Dissolve dl-2-dimethylamino-2-phenylethylamine, dihydrochloride (4.74 g.) in water (50 ml.), stir and cool with an ice-bath. Add 37% aqueous formaldehyde solution (2.0 ml.), stir for 10 minutes, then drip in a solution of potassium cyanide (1.30 g.) in water (20 ml.). Stir the cold solution for 1 hour, then cool further to 0° C. (ice-salt bath). Drip in a solution of sodium nitrite (1.4 g.) in water (15 ml.) followed by 5N aqueous HCl (8 ml.). Stir, then again drip in a solution of sodium nitrite (1.4 g.) in water (15 ml.) and continue stirring for 3 hours, allowing the reaction to warm to room temperature. Drip in 5N aqueous sodium hydroxide solution unitl a pH of 10 is attained. Quickly extract with diethyl ether, then dry and evaporate the solvent in vacuo. Pump dry, then treat the oil in diethyl ether with decolorizing carbon, filter and evaporate, then pump to obtain dl-[[2-(dimethylamino)-2-phenylethyl]nitrosoamino]acetonitrile as an oil (about 3 g.). To characterize this product dissolve a sample (313 mg.) in methylene chloride, treat with 5N isopropanolic-HCl (1 ml.), then evaporate the solvent in vacuo. Crystallize the residue from acetone, filter to obtain the hydrochloride salt (210 mg.); m.p. 164°–166° C.

Analysis for: $C_{12}H_{16}N_4O \cdot HCl$. Calculated: C, 53.63; H, 6.38; N, 20.85%. Found: C, 53.51; H, 6.34; N, 21.31%.

Dissolve [[2-(dimethylamino)-2-phenylethyl]nitrosoamino]-acetonitrile (4.43 g.) in methylene chloride, add excess 5N isopropanolic—HCl (8 ml.) and let stand overnight. Filter to obtain 1.86 g. of the crude title product, m.p. 150° C. (dec).

Combine the product of several runs (3.34 g.), dissolve in 70% aqueous ethanol, treat with decolorizing carbon, filter and dilute the filtrate with isopropanol. Evaporate the solvents in vacuo, cover the remaining glassy material with methylene chloride and let stand to crystallize. Filter to obtain 2.62 g. of the title product as the hydrochloride hydrate, m.p. 157°–158° C. (dec).

Analysis for: $C_{12}H_{17}ClN_4O \cdot HCl \; 1.5H_2O$. Calculated: C, 43.38; H, 6.37; N, 16.86%. Found: C, 43.66; H, 5.85; N, 17.49%.

The antihypertensive activity of d,l-5-amino-3-(2-(dimethylamino)-2-phenylethyl)-1,2,3-oxadiazolium chloride, hydrochloride, which compound is representative in its activity of the other compounds of this invention, was established by orally administering the compound to a group of unanesthetized, spontaneously hypertensive rats while indirectly measuring their systolic blood pressure employing a Decker Caudal Plethysmograph. A decrease of 51 mmHg blood pressure was found at 1.5 hours after oral administration of 50 mg/kg of compound and a decrease of 40 mmHg at 1.5 and 4 hours at 25 mg/kg was demonstrated.

Thus, the antihypertensive agents of this invention are useful in treatment of hypertension and as such they may be administered to a patient suffering from hypertension, orally or parenterally, in an amount of from about 25 to 50 mg/kg or more, based upon the test results, in single or divided doses. The dosage regimen and route of administration may be varied by the attending physician to achieve the desired response depending upon the condition of the patient relative to age, severity of hypertensive state, etc.

What is claimed is:

1. A compound of the formula:

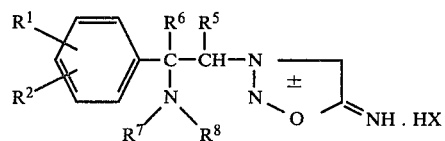

in which $R^1$ and $R^2$ are, independently, hydrogen, alkyl of 1 to 6 carbon atoms, alkoxy of 1 to 6 carbon atoms, halo, perfluoroalkyl of 1 to 3 carbon atoms, nitro, alkanoyl of 2 to 4 carbon atoms, or alkoxycarbonyl of 2 to 4 carbon atoms;

$R^5$ and $R^6$ are, independently, hydrogen or methyl;

$R^7$ and $R^8$ are, independently, alkyl of 1 to 4 carbon atoms, or when taken with the nitrogen atom to which they are attached, form a piperidinyl, pyrolidinyl, morpholinyl, N-alkyl piperazinyl in which the alkyl group contains from 1 to 6 carbon atoms or N-phenylpiperazinyl group; and X is the anion of a strong acid having a pKa below 2; or a pharmaceutically acceptable acid addition salt thereof.

2. A compound of claim 1 of the formula:

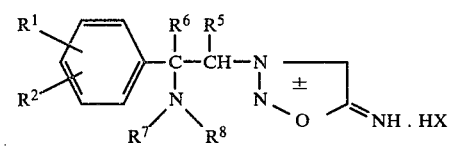

in which $R^1$ and $R^2$ are, independently, hydrogen, alkyl of 1 to 3 carbon atoms, alkoxy of 1 to 3 carbon atoms, chloro, bromo, fluoro, perfluoroalkyl of 1 to 3 carbon atoms, nitro, alkanoyl of 2 to 4 carbon atoms or alkoxycarbonyl of 2 to 4 carbon atoms;

$R^5$ and $R^6$ are, independently, hydrogen or methyl;
$R^7$ and $R^8$ are, independently, alkyl of 1 to 3 carbon atoms or when taken with the nitrogen atom to which they are attached, form a piperidinyl, pyrolidinyl, morpholinyl, N-alkylpiperazinyl in which the alkyl group contains from 1 to 3 carbon atoms on N-phenylpiperazinyl group; and
X is an anion of a strong acid having a pKa below 2;

or a pharmaceutically acceptable acid addition salt thereof.

3. A compound of claim 1 which is 5-amino-3-[2-(dimethylamino)-2-phenylethyl]-1,2,3-oxadiazolium chloride or a pharmaceutically acceptable acid addition salt thereof.

* * * * *